(12) United States Patent
Eisinger (10) Patent No.: US 9,133,081 B2
(45) Date of Patent: Sep. 15, 2015

(54) METHODS FOR THE REMOVAL OF IMPURITIES FROM POLYMERIZATION FEED STREAMS

(75) Inventor: Ronald S. Eisinger, Charleston, WV (US)

(73) Assignee: Univation Technologies, LLC, Houston, TX (US)

( * ) Notice: Subject to any disclaimer, the term of this patent is extended or adjusted under 35 U.S.C. 154(b) by 407 days.

(21) Appl. No.: 12/743,010

(22) PCT Filed: Nov. 12, 2008

(86) PCT No.: PCT/US2008/012702
§ 371 (c)(1),
(2), (4) Date: May 14, 2010

(87) PCT Pub. No.: WO2009/064411
PCT Pub. Date: May 22, 2009

(65) Prior Publication Data
US 2010/0261856 A1    Oct. 14, 2010

Related U.S. Application Data

(60) Provisional application No. 61/003,239, filed on Nov. 15, 2007.

(51) Int. Cl.
| | |
|---|---|
| *C07C 7/148* | (2006.01) |
| *C08F 10/02* | (2006.01) |
| *C08F 110/02* | (2006.01) |

(52) U.S. Cl.
CPC .............. *C07C 7/1485* (2013.01); *C08F 10/02* (2013.01); *B01D 2251/102* (2013.01); *B01D 2255/20761* (2013.01); *B01D 2257/104* (2013.01); *B01D 2257/502* (2013.01); *C08F 110/02* (2013.01); *Y02C 10/04* (2013.01)

(58) Field of Classification Search
None
See application file for complete search history.

(56) References Cited

U.S. PATENT DOCUMENTS

| | | | |
|---|---|---|---|
| 2,837,587 A | 6/1958 | Paul et al. | 585/251 |
| 3,432,573 A | 3/1969 | Keil | 585/518 |
| 3,523,110 A | 8/1970 | Eichenbaum | 526/68 |
| 3,779,712 A | 12/1973 | Calvert et al. | 422/219 |
| 3,792,105 A | 2/1974 | Siegmann | 585/854 |
| 4,003,172 A | 1/1977 | Pawl | 52/279 |
| 4,011,382 A | 3/1977 | Levine et al. | 526/96 |
| 4,019,879 A | 4/1977 | Rabo et al. | 95/140 |
| 4,025,321 A | 5/1977 | Anderson et al. | 95/123 |
| 4,034,062 A | 7/1977 | Krueger | 423/219 |
| 4,034,065 A | 7/1977 | Kasai et al. | 423/700 |

(Continued)

FOREIGN PATENT DOCUMENTS

| | | |
|---|---|---|
| CA | 2045060 | 1/1992 |
| EP | 0102503 | 3/1984 |

(Continued)

OTHER PUBLICATIONS

Abstract for Esso Res & Eng Co. CA 877294 (1979).*

(Continued)

*Primary Examiner* — Melvin C Mayes
*Assistant Examiner* — Sheng H Davis
(74) *Attorney, Agent, or Firm* — Brooks, Cameron & Huebsch, PLLC (57) ABSTRACT

Methods for the removal of impurities, for example, carbon monoxide, from a polymerization feed streams are provided.

13 Claims, 4 Drawing Sheets

(56) References Cited

U.S. PATENT DOCUMENTS

| | | | | |
|---|---|---|---|---|
| 4,077,904 A | 3/1978 | Noshay et al. | | 502/152 |
| 4,115,639 A | 9/1978 | Brown et al. | | 526/130 |
| 4,302,565 A | 11/1981 | Goeke et al. | | 526/88 |
| 4,302,566 A | 11/1981 | Karol et al. | | |
| 4,482,687 A | 11/1984 | Noshay et al. | | |
| 4,521,387 A | 6/1985 | Broecker et al. | | 423/210 |
| 4,530,910 A | 7/1985 | Mross et al. | | 502/24 |
| 4,543,399 A | 9/1985 | Jenkins, III et al. | | 526/70 |
| 4,560,671 A | 12/1985 | Gross et al. | | 502/105 |
| 4,564,605 A | 1/1986 | Collomb-Ceccarini et al. | | 502/110 |
| 4,585,840 A | 4/1986 | Gross et al. | | 526/159 |
| 4,587,114 A | 5/1986 | Hirai et al. | | 423/247 |
| 4,588,790 A | 5/1986 | Jenkins, III et al. | | 526/70 |
| 4,621,592 A | 11/1986 | McInerney | | |
| 4,621,952 A | 11/1986 | Aronson | | 406/138 |
| 4,666,990 A | 5/1987 | Candlin et al. | | |
| 4,696,682 A | 9/1987 | Hirai et al. | | 95/140 |
| 4,721,763 A | 1/1988 | Bailly et al. | | 526/88 |
| 4,803,251 A | 2/1989 | Goode et al. | | 526/59 |
| 4,869,883 A | 9/1989 | Thorogood et al. | | 423/219 |
| 4,879,359 A | 11/1989 | Chamla et al. | | 526/105 |
| 4,917,711 A | 4/1990 | Xie et al. | | 95/106 |
| 4,920,088 A * | 4/1990 | Kolts | | 502/326 |
| 4,933,149 A | 6/1990 | Rhee et al. | | 422/131 |
| 4,960,741 A | 10/1990 | Bailly et al. | | 502/10 |
| 4,994,534 A | 2/1991 | Rhee et al. | | 526/88 |
| RE33,683 E | 9/1991 | Allen et al. | | 502/107 |
| 5,047,468 A | 9/1991 | Lee et al. | | 525/53 |
| 5,064,918 A | 11/1991 | Malanga | | |
| 5,093,415 A | 3/1992 | Brady, III et al. | | 525/53 |
| 5,200,477 A | 4/1993 | Baker et al. | | 526/74 |
| 5,270,408 A | 12/1993 | Craddock, III et al. | | 526/82 |
| 5,288,933 A | 2/1994 | Kao et al. | | 585/513 |
| 5,290,745 A | 3/1994 | Jorgensen et al. | | 502/109 |
| 5,317,036 A | 5/1994 | Brady, III et al. | | 523/223 |
| 5,318,935 A | 6/1994 | Canich et al. | | 502/117 |
| 5,352,749 A | 10/1994 | DeChellis et al. | | 526/68 |
| 5,405,901 A | 4/1995 | Daniell et al. | | 525/53 |
| 5,428,118 A | 6/1995 | Painter et al. | | 526/74 |
| 5,453,471 A | 9/1995 | Bernier et al. | | 526/68 |
| 5,461,123 A | 10/1995 | Song et al. | | 526/74 |
| 5,518,973 A | 5/1996 | Miro et al. | | 502/125 |
| 5,525,678 A | 6/1996 | Mink et al. | | 525/246 |
| 5,529,763 A | 6/1996 | Peng et al. | | 423/246 |
| 5,625,116 A * | 4/1997 | Flammini et al. | | 585/848 |
| 5,627,242 A | 5/1997 | Jacobsen et al. | | 526/60 |
| 5,728,782 A | 3/1998 | Brady et al. | | 526/63 |
| 5,731,381 A | 3/1998 | Apecetche et al. | | 526/83 |
| 5,744,556 A | 4/1998 | Keller et al. | | 526/131 |
| 5,834,571 A | 11/1998 | Bernier et al. | | 526/68 |
| 5,879,805 A | 3/1999 | Brady et al. | | 428/407 |
| 5,889,128 A | 3/1999 | Schrock et al. | | 526/107 |
| 5,907,076 A | 5/1999 | Ou et al. | | 585/800 |
| 5,912,309 A | 6/1999 | Lee et al. | | 526/74 |
| 6,004,677 A | 12/1999 | Cann et al. | | 428/407 |
| 6,011,128 A | 1/2000 | Eisinger et al. | | 526/130 |
| 6,063,877 A | 5/2000 | Kocian et al. | | 526/61 |
| 6,093,285 A | 7/2000 | Fernald et al. | | 203/14 |
| 6,096,840 A | 8/2000 | Bernier et al. | | 526/68 |
| 6,111,162 A | 8/2000 | Rossini et al. | | 585/824 |
| 6,214,903 B1 | 4/2001 | Eisinger et al. | | 523/330 |
| 6,255,420 B1 | 7/2001 | Dietz, III et al. | | 526/185 |
| 6,261,528 B1 | 7/2001 | Carrea et al. | | 423/230 |
| 6,271,325 B1 | 8/2001 | McConville et al. | | 526/217 |
| 6,278,033 B1 | 8/2001 | Flick et al. | | 585/262 |
| 6,300,429 B1 | 10/2001 | Spriggs et al. | | 526/62 |
| 6,306,981 B1 | 10/2001 | Brown et al. | | 526/68 |
| 6,333,389 B2 | 12/2001 | Whiteker et al. | | 526/161 |
| 6,384,156 B1 | 5/2002 | Bernier et al. | | 526/88 |
| 6,441,107 B1 | 8/2002 | Muruganandam et al. | | 526/60 |
| 6,472,483 B1 | 10/2002 | Goode et al. | | 526/88 |
| 6,562,905 B1 | 5/2003 | Nummila-Pakarinen et al. | | 525/191 |
| 6,627,713 B2 | 9/2003 | Bernier et al. | | 526/137 |
| 6,986,797 B1 * | 1/2006 | Clawson et al. | | 48/102 A |
| 6,987,152 B1 | 1/2006 | Eisinger et al. | | 526/77 |
| 7,314,965 B2 * | 1/2008 | Vorberg et al. | | 585/845 |
| 7,622,421 B2 * | 11/2009 | Deevi et al. | | 502/343 |
| 2002/0114746 A1 * | 8/2002 | Roark et al. | | 422/177 |
| 2002/0131915 A1 * | 9/2002 | Shore et al. | | 422/177 |
| 2003/0236365 A1 | 12/2003 | Tian et al. | | 526/72 |
| 2004/0020124 A1 * | 2/2004 | Russell et al. | | 48/198.3 |
| 2004/0052708 A1 | 3/2004 | Rao | | 423/219 |
| 2005/0241478 A1 | 11/2005 | Junicke et al. | | 95/140 |
| 2006/0289024 A1 * | 12/2006 | Deevi et al. | | 131/363 |
| 2008/0166605 A1 * | 7/2008 | Arps et al. | | 429/15 |
| 2009/0269269 A1 * | 10/2009 | White et al. | | 423/437.2 |

FOREIGN PATENT DOCUMENTS

| | | |
|---|---|---|
| EP | 0103120 | 3/1984 |
| EP | 0370617 A | 5/1990 |
| EP | 0231102 | 3/1995 |
| EP | 0662595 | 9/1997 |
| EP | 0703246 | 1/2002 |
| EP | 0966508 | 2/2003 |
| GB | 1553383 | 9/1979 |
| GB | 2105355 | 3/1983 |
| WO | WO 98/41597 | 9/1998 |
| WO | WO 99/01460 | 1/1999 |
| WO | WO 2006/76096 | 7/2006 |

OTHER PUBLICATIONS

Katz, Morris; "Heterogeneous Oxidation of Carbon Monoxide," Advances in Catalysis, vol. V, p. 177 (1953).

Mohammed M. et al "Understanding Propylene Polymerization Mechanism(s) Using Two-State ansa-Metallocene Catalysts" A Thesis presented to the Uniterstity of Waterloo, Ontario, Canada, 2001.

Pillai U R et al: "Room temperature oxidation of carbon monoxide over copper oxide catalyst" Applied Catalysis B: Environmental, Elsevier, vol. 64, No. 1-2, Apr. 18, 2006, pp. 146-151, XP02514115.

Reid, J.A. and McPhaul, D.R., *Control Contaminants in Olefin Feedstocks and Products*, Hydrocarbon Processing (Jul. 1996), pp. 45-53 [pp. 49 and 51 are ads].

Reid, J.A. and McPhaul, D.R., Part 2 Control Contaminants in Olefin Feedstocks and Products, Hydrocarbon Processing (Sep. 1996), pp. 128-136 [pp. 129, 131, 132 and 135 are ads].

United Catalysts Inc., G-66B for Co and O2 Removal, pp. 1-11.

* cited by examiner

METHODS FOR THE REMOVAL OF IMPURITIES FROM POLYMERIZATION FEED STREAMS

CROSS REFERENCE TO RELATED APPLICATIONS

This application claims the benefit of Ser. No. 61/003,239, filed Nov. 15, 2007, the disclosure of which is incorporated by reference in its entirety.

FIELD OF THE INVENTION

The invention generally relates to the removal of impurities from polymerization feed streams. In particular, this disclosure relates to the removal of carbon monoxide and oxygen from polymerization feed streams by catalytically reacting the carbon monoxide and oxygen.

BACKGROUND

Processes that polymerize olefins, for example, ethylene, propylene, butene, hexene, octene, etc. often use high-activity catalysts that may be sensitive to poisons in the polymerization feed stream. Common poisons that decrease catalyst activity or cause operating problems in the polymerization process include, among others, oxygen ($O_2$) and carbon monoxide (CO). Copper (Cu) in its various oxidation states, particularly copper oxide (CuO), is useful for removing certain poisons, such as carbon monoxide, through catalytic oxidation of carbon monoxide to carbon dioxide ($CO_2$). However, the oxidation of carbon monoxide by copper oxide is typically accomplished at temperatures well above ambient temperature to effectively remove the carbon monoxide. For example, a review in Katz, Morris, "Heterogeneous Oxidation of Carbon Monoxide," in *Advances in Catalysis*, Vol. V, p. 177 (1953), indicates that the oxidation of carbon monoxide by unpromoted copper oxide may not commence until about 200° C.

Purification processes may require heating and cooling the feed olefin to effectively remove the catalyst poisons from the olefin feed, thus consuming significant energy to process the feed olefin. For example, a reactor system may receive olefins at about ambient temperatures (about 0 to about 35° C.). The olefin purification train may have individual beds for removal of oxygen and carbon monoxide followed by an adsorbent bed(s) for removal of water and carbon dioxide. The oxygen and carbon monoxide removal beds may operate at about 100° C. or higher, while the adsorbent beds typically operate at ambient temperatures. This means the feed olefin must first be heated to 100° C. or higher, then cooled again to near-ambient temperatures.

One catalyst known for removing carbon monoxide is a mixture of copper oxide and manganese dioxide known as hopcalite. Some copper oxide and manganese dioxide catalysts are thought to remove carbon monoxide from dry air by reaction at ambient temperature as low as −20° C. U.S. Pat. No. 2,837,587 discusses the removal of carbon monoxide from a mixture of olefins and hydrogen at 10 to 90° C. and at space velocity up to 1000 $h^{-1}$ with a hopcalite catalyst. However, mixtures of copper oxide and manganese dioxide may hydrogenate some olefins, such as ethylene, making it undesirable for many polymerization processes.

U.S. Pat. No. 5,907,076 discloses a copper oxide catalyst to oxidize hydrogen and carbon monoxide contained in a hydrocarbon stream at a temperature as low as 40° C. The Examples of the '076 patent demonstrate an oxidation temperature of 104° C. The '076 patent indicates multiple scenarios of operation. In one scenario, the carbon monoxide is reacted with less than a stoichiometric amount of oxygen, which results in little oxygen passing through the removal bed, but some carbon monoxide passing through the removal bed. In a subsequent step, the remaining carbon monoxide is removed by reacting carbon monoxide and water over a separate metal oxide catalyst to form carbon dioxide. In another scenario, the stream is denuded of carbon monoxide by reacting the carbon monoxide with a copper oxide catalyst with 100 to 500% of the stoichiometric amount of oxygen present, but results in oxygen passing through the removal bed.

European Patent 0 966 508 A discusses a process comprising at least two steps for removing impurities, such as oxygen, in an olefin stream. The first step teaches the hydrogenation of oxygen and other impurities using a hydrogenation catalyst containing silver and palladium. The second step teaches removing at least part of the residual oxygen—by oxidation with carbon monoxide with a copper/copper oxide catalyst. The disclosure teaches that during the reaction of carbon monoxide and oxygen, the temperature should be at least 15° C. and preferably 40° C. or more.

U.S. Patent Application Publication No. 2005/0241478 teaches the adsorption of carbon monoxide with a composition containing copper, zinc, and zirconium. The adsorption is effective at ambient temperature, but capacity appears to be low.

U.S. Pat. No. 4,869,883 employs a copper oxide catalyst to oxidize carbon monoxide at a temperature of from 150 to 250° C.

Other background references include U.S. Pat. Nos. 4,019,879, 4,034,062, 4,034,065, 4,587,114, 4,696,682, 4,917,711, 5,529,763, 6,278,033, 6,987,152; WO 98/41597; CA 2 045 060; and European Patent 6 62 595 A.

SUMMARY

In a class of embodiments, the invention provides for a method for removing carbon monoxide from a polymerization feedstream while the feed stream is near ambient temperature. In another class of embodiments, the invention also provides for a method of polymerization wherein carbon monoxide is removed from a polymerization feedstream while the feed stream is near ambient temperatures.

For example, one class of embodiments provide for a method of removing carbon monoxide from a feed fluid comprising the steps of: providing a feed fluid comprising carbon monoxide; measuring an oxygen concentration and a carbon monoxide concentration in the feed fluid or in a reacting fluid; combining an oxygen-containing fluid with the feed fluid to form the reacting fluid, wherein an amount of oxygen-containing fluid combined with the feed fluid is controlled to establish an $O_2$/CO molar ratio in the reacting fluid of greater than about 0.5:1; and passing the reacting fluid over a reduced copper-oxide catalyst at an operating temperature of less than about 40° C. to form a purified fluid, wherein oxygen and carbon monoxide contained in the reacting fluid are reacted in the presence of the reduced copper-oxide catalyst to form carbon dioxide.

In any embodiment herein, the purified fluid may comprise less than about 0.20 ppm by volume of carbon monoxide.

In one or more embodiments herein, the reduced copper-oxide catalyst also removes oxygen in the reacting fluid by reacting oxygen with reduced copper such that the purified fluid comprises less than about 0.20 ppm by volume of oxygen.

In any embodiment herein, the reaction of oxygen with carbon monoxide over reduced copper may occur in a single packed bed of reduced copper-oxide catalyst.

In one or more embodiments herein, the purified fluid may comprise less than about 0.10 ppm by volume of carbon monoxide and less than about 0.10 ppm by volume of oxygen.

In one or more embodiments herein, the reduced copper-oxide catalyst may comprise copper oxide and zinc oxide.

In one or more embodiments herein, the feed fluid may be ethylene, propylene, or nitrogen.

In one or more embodiments herein, the $O_2/CO$ molar ratio in the reacting fluid may be equal to or greater than about 1:1, 2:1, 3:1, or 3.3:1.

In one or more embodiments herein, an operating temperature of the reacting fluid passing over the reduced copper-oxide catalyst is less than about 35° C., or may be between about 0 to about 30° C.

In one or more embodiments herein, the reacting fluid is a gas, and a space velocity of the reacting fluid over the reduced copper-oxide catalyst is between about 1,000 to about 10,000 $h^{-1}$.

In one class of embodiments, the invention provides a method of removing carbon monoxide from a feed fluid comprising the steps of: providing a feed fluid comprising carbon monoxide; combining an oxygen-containing fluid with the feed fluid to form a reacting fluid, wherein an amount of oxygen-containing fluid combined with the feed fluid is controlled in real-time to establish an $O_2/CO$ molar ratio in the reacting fluid of greater than about 0.5:1; passing the reacting fluid over the reduced copper-oxide catalyst at an operating temperature of less than about 40° C. to form a purified fluid, wherein oxygen and carbon monoxide contained in the reacting fluid are reacted in the presence of the reduced copper-oxide catalyst to form carbon dioxide; measuring a real-time carbon monoxide concentration in the purified fluid; and increasing the amount of oxygen-containing fluid combined with the feed fluid in response to an increase over time in the real-time carbon monoxide concentration measured in the purified fluid.

In another class of embodiments, the invention provides for a method of removing carbon monoxide from a feed fluid comprising the steps of: providing a feed fluid comprising carbon monoxide; obtaining a real-time operating temperature of a reacting fluid; combining an oxygen-containing fluid with the feed fluid to form the reacting fluid, wherein an amount of oxygen-containing fluid combined with the feed fluid is determined in real time and controlled in real time based on the real-time operating temperature of the feed fluid passing over the reduced copper-oxide catalyst, the specified carbon monoxide concentration in the feed fluid, and a real-time flow rate of the reacting fluid over the reduced copper-oxide catalyst to form a purified fluid, wherein oxygen and carbon monoxide contained in the reacting fluid are reacted in the presence of the reduced copper-oxide catalyst to form carbon dioxide.

In one or more embodiments herein, an operating temperature of the reacting fluid passing over the reduced copper-oxide catalyst is less than about 40° C.

One class of embodiments provides a method of removing carbon monoxide from a feed fluid comprising the steps of: providing a feed fluid comprising carbon monoxide and oxygen; measuring an oxygen concentration and a carbon monoxide concentration in the feed fluid in real time; passing the feed fluid over a reduced copper-oxide catalyst to form a purified fluid, wherein oxygen and carbon monoxide contained in the feed fluid are reacted in the presence of the reduced copper-oxide catalyst to form carbon dioxide; and controlling a real-time operating temperature of the feed fluid passing over the reduced copper-oxide catalyst at a preferred operating temperature; and wherein the preferred operating temperature is determined based on a real-time molar ratio of $O_2/CO$ in the feed fluid.

In one embodiment, the preferred operating temperature is determined based on the real-time molar ratio of $O_2/CO$ in the feed fluid, and a real-time flow rate of the feed fluid over the reduced copper-oxide catalyst.

In another embodiment, the reduced copper-oxide catalyst also removes oxygen in the feed fluid by reacting oxygen with the reduced copper-oxide catalyst such that the purified fluid comprises less than about 0.20 ppm by volume of oxygen, and wherein the reactions of oxygen ($O_2$) with carbon monoxide and reduced copper occur in a single packed bed of reduced copper-oxide catalyst.

In yet another embodiment, the feed fluid is a gas, and a space velocity of the feed fluid over the reduced copper-oxide catalyst is between about 1,000 to about 10,000 $h^{-1}$.

In one or more embodiments, the preferred operating temperature is determined based on the real-time molar ratio of $O_2/CO$ in the feed fluid, and a real-time flow rate of the reacting fluid over the reduced copper-oxide catalyst.

In one or more embodiments, the $O_2/CO$ molar ratio in the feed fluid is equal to or greater than about 0.5:1, 1:1. 2:1, 3:1, or 3.3:1.

Another class of embodiments provides a method for olefin polymerization, comprising: providing a feed fluid comprising more than about 0.2 ppm by volume of carbon monoxide; measuring an oxygen concentration and a carbon monoxide concentration in the feed fluid; combining an oxygen-containing fluid with the feed fluid to form a reacting fluid, wherein an amount of oxygen-containing fluid combined with the feed fluid is controlled to establish an $O_2/CO$ molar ratio in the reacting fluid of greater than about 0.5:1; passing the reacting fluid over a reduced copper-oxide catalyst at an operating temperature of less than about 40° C. to form a purified fluid, wherein the reduced copper-oxide catalyst comprises copper oxide and zinc oxide, wherein oxygen and carbon monoxide contained in the reacting fluid are reacted in the presence of the reduced copper-oxide catalyst to form carbon dioxide, and wherein the purified fluid comprises less than about 0.2 ppm by volume of carbon monoxide; and passing the purified fluid to a polymerization reactor.

DETAILED DESCRIPTION

Before the present compounds, components, compositions, and/or methods are disclosed and described, it is to be understood that unless otherwise indicated this invention is not limited to specific compounds, components, compositions, reactants, reaction conditions, structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified.

Generally, embodiments disclosed herein relate to a method of removing carbon monoxide from a feed stream to a polymerization process, and a method of olefin polymerization wherein carbon monoxide is removed from a feed stream to the polymerization process. More specifically, embodiments disclosed herein relate to a method of removing carbon monoxide from a feed stream to a polymerization process while the feed stream is near ambient temperatures. The embodiments herein further relate to the removal of carbon monoxide and oxygen from a polymerization feed stream while the feed stream is near ambient temperatures.

The term "impurities" as used herein refers to a component or compound that reduces the activity of a polymerization catalyst or adversely affects the operability of the olefin polymerization process. Illustrative impurities include, but are not limited to, oxygen, carbon monoxide, carbon dioxide, hydrocarbons having oxygen-containing functional groups such as alcohols, aldehydes, ketones, organic acids, some esters and peroxides, water, sulfur-containing compounds, and arsine. Illustrative sulfur-containing compounds include, but are not limited to hydrogen sulfide, carbonyl sulfide, and mercaptans having the general formula R—SH where R is an alkyl group having 1 to 20 carbon atoms.

The term "feed fluid" as used herein refers to a raw material, either gas phase or liquid phase, used in a polymerization process producing a polymer product. For example, a feed fluid may be any olefin monomer including substituted and unsubstituted alkenes having two to 10 carbon atoms, such as ethylene, propylene, 1-butene, 1-pentene, 1-hexene, 1-octene, 1-decene, 1-dodecene, styrene, and derivatives and mixtures thereof. The feed fluid may also be a gas stream such as nitrogen or hydrogen. The feed fluid may further be one or more nonreactive alkanes that are condensable in the polymerization process for removing the heat of reaction. Illustrative nonreactive alkanes include, but are not limited to, propane, butane, isobutane, pentane, isopentane, hexane, isomers thereof and derivatives thereof.

The term "packed bed" as used herein refers to a bed of material for impurity removal (i.e. "purification material") that is fixed within a container or vessel. A packed bed may comprise one or more catalysts, absorbents, adsorbents, reactants, and any combination thereof. Each packed bed may be contained in a single container, such as a vertical pressure-rated vessel, or may be split between two or more contiguous vessels. The term "single packed bed" refers to a contiguous bed of one purification material in a packed bed. In other words, the feed fluid only passes through the purification material at one step in a series of purification steps. The term "single packed bed" also includes two or more packed beds of the same purification material arranged in parallel.

The term "space velocity" (SV) as used herein refers to the volumetric flow rate of a fluid through a packed bed. All values of SV herein are expressed in as $h^{-1}$ (inverse hours).

The term "ambient temperature" as used herein refers to the temperature of the environment in which any physical or chemical event occurs, unless otherwise specified. The term "at" or "near" "ambient temperature" as used herein refers to the temperature of the environment in which any physical or chemical event occurs plus or minus ten degrees, alternatively, five degrees, alternatively, three degrees, alternatively two degrees, and alternatively, one degree, unless otherwise specified.

All concentrations expressed herein are concentrations in terms of parts per million by volume unless otherwise stated.

It has been surprisingly discovered that carbon monoxide can be removed from a polymerization feedstream while the feedstream is at temperatures of less than about 40° C. by passing the feedstream over a reduced copper-oxide catalyst in the presence of greater than a stoichiometric ratio of oxygen to carbon monoxide. Particularly surprising is the finding that the carbon monoxide can be removed to levels of less than about 0.2 ppm by volume at temperatures of less than about 40° C. by maintaining the $O_2/CO$ ratio in the feed fluid of greater than about 0.5:1.

Figure 1:
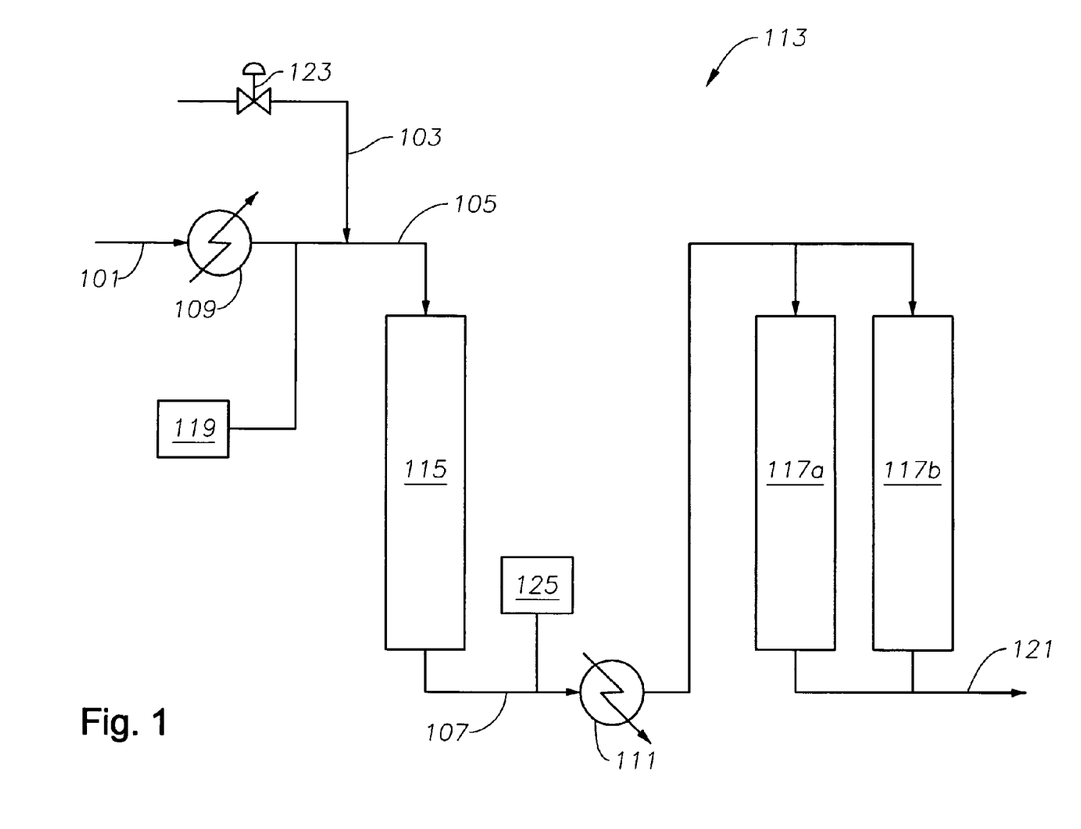
FIG. 1 is a schematic drawing of an exemplary purification section of a polymerization reactor system.

Referring to FIG. 1, one class of embodiments are directed to a method of removing carbon monoxide from a feed fluid by: providing a feed fluid 101 comprising carbon monoxide; measuring an oxygen concentration and a carbon monoxide concentration in the feed fluid 101; combining an oxygen-containing fluid 103 with the feed fluid 101 to form a reacting fluid 105 wherein an amount of oxygen-containing fluid 103 combined with the feed fluid 101 is controlled to establish an $O_2/CO$ molar ratio in the reacting fluid 105 of greater than about 0.5:1; and passing the reacting fluid 105 over a reduced copper-oxide catalyst at an operating temperature of less than about 40° C. to form a purified fluid 107, wherein oxygen and carbon monoxide contained in the reacting fluid 105 are reacted in the presence of the reduced copper-oxide catalyst to form carbon dioxide.

By removing the carbon monoxide at temperatures near ambient, significant investment and energy savings are realized. For example, a pre-heater 109 and a post cooler 111 may be eliminated reducing both capital expenditures and operating expenses. Furthermore, the current invention provides a method of removing both carbon monoxide and oxygen in the same catalyst bed, thus further reducing capital and operating expenses. In any embodiment, the current invention provides a method of removing carbon monoxide from a feed fluid 101 comprising carbon monoxide at temperatures less than about 40° C. In other embodiments, the carbon monoxide may be removed at temperatures of less than about 35° C., less than about 30° C., or at temperatures between about 0 and 40° C. In still other embodiments, the carbon monoxide may be removed at temperatures of between about 0 and 30° C.

FIG. 1 schematically depicts an exemplary purification section 113 for removing impurities according to embodiments described herein. The purification section 113 removes one or more impurities from a feed fluid 101 prior to the feed fluid 101 passing to a polymerization process. The purification section 113 may include one or more vessels that each contains one or more packed beds of purification material for impurity removal. As shown in FIG. 1, the purification section 113 may include a first packed bed 115 for removing one or more impurities and a second packed bed 117a,b for removing one or more other impurities not removed in the first packed bed 115.

The feed fluid 101 may include carbon monoxide and one or more additional impurities, such as oxygen and water for example, in an amount that exceeds the tolerance level of the polymerization catalyst. The carbon monoxide and other impurities are removed in the purification section 113. For example, the feed fluid 101 may comprise more than about 0.2 ppm by volume (ppmv) of carbon monoxide, 0.1 ppm by volume (ppmv) of oxygen, and 0.3 ppmv of water. In one or more embodiments, the feed fluid 101 may include more than 1.0 ppm by volume (ppmv) of carbon monoxide, 0.5 ppm by volume (ppmv) of oxygen and 0.5 ppmv of water. In other embodiments, the feed fluid 101 may include about 0.2 ppmv to about 10 ppmv of carbon monoxide, about 0.1 ppmv to about 10 ppmv of oxygen, and of from about 0.3 ppmv to about 10 ppmv of water.

The amount of oxygen, if any, and the amount of carbon monoxide in the feed fluid 101 or in a reacting fluid 105 may be measured, for example, in real-time by an on-line feed purity analyzer 119, before the feed fluid 101 or reacting fluid 105 contacts the first packed bed 115 (analyzer shown in FIG. 1 samples the feed fluid). The on-line feed purity analyzer 119 may be any analyzer or combination of more than one analyzer with the ability to measure oxygen and carbon monoxide at levels that may be found in the feed fluid 101. For example, the analysis of carbon monoxide in the feed fluid 101 may be carried out periodically, for example every 2 to 15 minutes, using a gas chromatograph with flame ionization detector and methanator. Examples of analyzers for analysis of oxygen in the feed fluid 101 include the Delta F NANO Trace II and Teledyne Ultra Trace 3000, which have the ability to measure down to 0.001 ppmv oxygen in the gas phase, and are available commercially.

In some embodiments of the invention, an oxygen-containing fluid 103 may be combined with the feed fluid 101 to form the reacting fluid 105 with sufficient oxygen present as required by the invention. The oxygen-containing fluid 103 may be combined with the feed fluid 101 to form the reacting fluid 105 upstream of the first packed bed 115. Alternately, the oxygen-containing fluid 103 may be introduced into the reaction zone of the packed bed via one or a plurality of oxygen injection points (not shown) located within the reaction zone. The oxygen-containing fluid 103 may be oxygen or any oxygen-containing fluid 103 that is compatible with the process.

In some embodiments, the amount of oxygen-containing fluid 103 combined with the feed fluid 101 may be controlled by controlling the flow of the oxygen-containing fluid 103. The desired flow of oxygen-containing fluid 103 may be determined by first measuring the flow rate of feed fluid 101, reacting fluid 105, purified fluid 107, or a polymerization feed 121 (provided the selected stream reflects the flow rate of reacting fluid 105 through the first packed bed 115), then using the measurements of oxygen and carbon monoxide concentration in the feed fluid 101 or reacting fluid 105 to determine the $O_2/CO$ molar ratio upstream of where the oxygen-containing fluid 103 is added. The flow rate of oxygen-containing fluid 103 to be added to achieve the desired $O_2/CO$ ratio in the reacting fluid 105 may then be determined. In a class of alternative embodiments, oxygen and carbon monoxide concentrations may be measured downstream. One means of adding a small amount of oxygen to the feed fluid 101 is by feeding dry instrument air boosted to sufficient pressure. A flow control valve 123, logic to control the amount of airflow, and appropriate safety equipment may be needed. In any embodiment, the $O_2/CO$ molar ratio in the reacting fluid 105 may be greater than the stoichiometric amount required to react carbon monoxide and oxygen to form carbon dioxide, an $O_2/CO$ ratio of 0.5:1.

The reacting fluid 105 may then pass over a reduced copper-oxide catalyst contained in the first packed bed 115 at an operating temperature of less than about 40° C. to form a purified fluid 107. The oxygen and carbon monoxide contained in the reacting fluid 105 are reacted in the presence of the reduced copper-oxide catalyst to form carbon dioxide. In other embodiments, the reacting fluid 105 may be passed over the reduced copper-oxide catalyst at an operating temperature of less than about 35° C., less than about 30° C., or at operating temperatures between about 0 and 40° C. In still other embodiments, the reacting fluid 105 may be passed over the reduced copper-oxide catalyst at an operating temperature of between about 0 and about 30° C.

The oxygen and the carbon monoxide in the reacting fluid 105 may react in the presence of the reduced copper-oxide catalyst in the first packed bed 115 to form carbon dioxide, thus removing oxygen and carbon monoxide from the reacting fluid 105 to form the purified fluid 107 that exits the first packed bed 115. Without being bound to one particular theory, it is believed that the following reaction may occur:

$$CO + 1/2 O_2 \underset{Cu}{\rightarrow} CO_2 \qquad \text{[Equation 1]}$$

It is believed that as long as metallic copper is present, and oxygen is present, this catalyzed oxidation may occur. It was previously believed that the catalytic component for the reaction in Equation 1 was copper oxide (CuO).

$$CO + 1/2 O_2 \underset{CuO}{\rightarrow} CO_2 \qquad \text{[Equation 2]}$$

Further, the catalyzed reaction in Equation 2 was thought to require temperatures well above ambient to initiate.

As discussed above, a review in Katz, Morris, "Heterogeneous Oxidation of Carbon Monoxide," in *Advances in Catalysis*, Vol. V, p. 177 (1953) indicates that the oxidation of carbon monoxide by copper oxide, as shown in Equation 2, may not commence until about 200° C. This is why the conversion of carbon monoxide to carbon dioxide by reacting over copper according to Equation 1 at temperatures less than about 40° C. is surprising. Thus, in any embodiment of the current invention, the reduced copper-oxide catalyst may comprise a copper-oxide catalyst that is at least partly reduced to copper. The copper-oxide catalyst may comprise one or more metals supported on a metal oxide carrier. Metals may include copper and other metals and/or oxides of other metals such as zinc, palladium, platinum, gold and silver, as described in U.S. Pat. No. 6,278,033. Thus, in any embodiment, the copper-oxide catalyst may comprise copper oxide and zinc oxide. In any embodiment, the copper-oxide catalyst may be UT-2000 catalyst, which is obtainable from Univation Technologies, LLC. Other illustrative copper-oxide catalysts include the PolyMax 301 and PolyMax 302 catalysts, which are commercially available from Sud-Chemie AG. The copper-oxide catalysts may be reduced by treatment of the copper-oxide catalyst with hydrogen at elevated temperature after being placed in the packed bed using procedures known in the art.

In any embodiment, the first packed bed 115 may further include any additional material.

The purified fluid 107 exiting the first packed bed 115 will have most, if not essentially all, of the measurable carbon monoxide removed. In any embodiment, the purified fluid 107 may comprise less than about 0.20 ppmv carbon monoxide. In other embodiments, the purified fluid 107 may comprise less than about 0.10 ppmv carbon monoxide, or may be absent of any measurable level of carbon monoxide.

In one or more embodiments herein, the reduced copper-oxide catalyst may also remove oxygen in the reacting fluid 105 by reaction of oxygen with the reduced copper-oxide catalyst. The oxygen may combine with the reduced copper-oxide to form copper oxide as shown in Equation 3.

$$2\,Cu + O_2 \rightarrow 2\,CuO \qquad \text{[Equation 3]}$$

Without being bound to one particular theory, it is believed that the carbon monoxide and oxygen react over the reduced copper-oxide catalyst to remove the carbon monoxide by forming carbon dioxide according to Equation 1, and the oxygen reacts with the reduced copper-oxide catalyst to remove the excess oxygen as shown in Equation 3. Thus, in one or more embodiments herein, the oxygen and carbon monoxide may be removed in a single bed of reduced copper-oxide catalyst. The copper-oxide formed by the oxidation of the copper can be later re-reduced using a regeneration stream comprising hydrogen (not shown). The regeneration stream carries off the removed oxygen as water, leaving behind a reduced metal ready for additional oxygen removal. Additional details can be found in U.S. Pat. Nos. 6,278,033 and 6,987,152. This combination of carbon monoxide and oxygen removal allows more oxygen to be present in the reacting fluid 105 than stoichiometrically required to react the oxygen and carbon monoxide to remove all of the carbon monoxide. The net result is that in one or more embodiments herein, the purified fluid 107 may comprise less than about 0.20 ppmv of oxygen, less than about 0.10 ppmv of oxygen, or may be absent any measurable level of oxygen. Furthermore, the oxygen may be removed by the same catalyst as the carbon monoxide, for example in the same catalyst bed, at the same conditions, resulting in a purified effluent comprising less than about 0.2 ppm by volume oxygen, and less than about 0.2 ppm by volume carbon monoxide. In some embodiments, the purified fluid 107 may comprise less than about 0.10 ppmv of oxygen, and less than about 0.10 ppmv of carbon monoxide.

Another class of embodiments provides a method of removing carbon monoxide from a feed fluid 101 comprising the steps of: providing a feed fluid 101 comprising carbon monoxide; combining an oxygen-containing fluid 103 with the feed fluid 101 to form a reacting fluid 105, wherein an amount of oxygen-containing fluid 103 combined with the feed fluid 101 is controlled in real-time to establish an $O_2/CO$ molar ratio in the reacting fluid 105 of greater than about 0.5:1; passing the reacting fluid 105 over the reduced copper-oxide catalyst at an operating temperature of less than about 40° C. to form a purified fluid 107, wherein oxygen and carbon monoxide contained in the reacting fluid 105 are reacted in the presence of the reduced copper-oxide catalyst to form carbon dioxide; measuring a real-time carbon monoxide concentration in the purified fluid 107; and increasing the amount of oxygen-containing fluid 103 combined with the feed fluid 101 in response to an increase over time in the real-time carbon monoxide concentration measured in the purified fluid 107. In this embodiment, the carbon monoxide concentration in the purified fluid 107 may be measured in real time by an on-line purified feed fluid analyzer 125 to determine how much, if any, carbon monoxide is coming through the first packed bed 115. The purified feed fluid analyzer 125 may be any impurity analyzer or combination of impurity analyzers with the ability to measure oxygen and carbon monoxide at levels that may be found in the purified fluid 107. If this analysis shows carbon monoxide is present, or shows the carbon monoxide in the purified fluid 107 increasing over time, then the amount of oxygen-containing fluid 103 being combined with the feed fluid 101 may be increased to increase the $O_2/CO$ ratio in the reacting fluid 105, and thus the removal of carbon monoxide in the first packed bed 115. The result is that the level of carbon monoxide passing through the first packed bed 115 will be decreased. In this method, it may be desirable to reduce the flow of oxygen-containing fluid 103 periodically to determine if the carbon monoxide in the purified fluid 107 returns.

It was found that the reaction of carbon monoxide with oxygen proceeds further by increasing the $O_2/CO$ ratio in the reacting fluid 105 above the stoichiometric levels, that is, above 0.5:1. In addition, excess oxygen, for example, $O_2/CO$ ratios of greater than about 1:1, 2:1, 3:1, or 3.3:1, improve the removal of carbon monoxide from the reacting fluid 105. Furthermore, the reaction of carbon monoxide with oxygen proceeds further to completion at higher temperature and lower space velocity. An empirical model to quantify these relationships is:

$$\text{Fraction of CO removed} = 1 - e^{[-2.261 - 0.866*(O2/CO)in - 0.032*T + 0.00065*SV - 0.14*(CO)in]} \quad \text{[Equation 4]}$$

where T is temperature in °C., SV is space velocity expressed as $h^{-1}$ (inverse hours), $(O_2/CO)_{in}$ is the molar ratio of oxygen to carbon monoxide in the reacting fluid 105, and $(CO)_{in}$ is the carbon monoxide concentration in the reacting fluid 105 expressed in units of ppm by volume. In some embodiments, $(CO)_{in}$ may also be carbon monoxide concentration in the feed fluid 101 expressed in units of ppm by volume, although this introduces a very small error in the results. Space velocity is the volumetric gas flow rate at 1 atmosphere and 21° C. divided by the packed bed volume. Equation 4 may be used to predict process conditions required to achieve desired purity levels in the purified fluid 107. An example of how the Fraction of CO removal is determined is as follows: a feed fluid 101 containing carbon monoxide at the limit of a typical ethylene specification of 5 ppmv may be assumed. Assuming an aim concentration of carbon monoxide in purified ethylene of less than about 0.2 ppmv, the fraction of carbon monoxide to be removed is 1−0.2/5=0.96.

Figure 2:
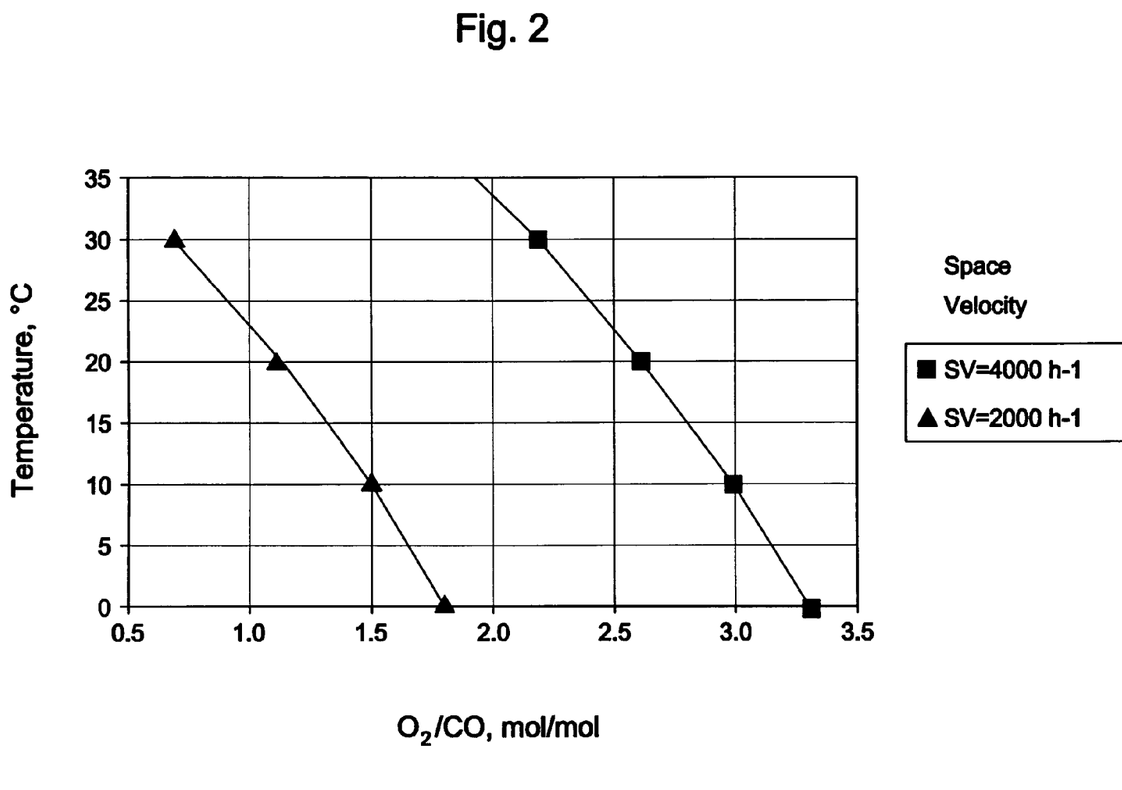
FIG. 2 is a graph showing the correlation of temperature and $O_2/CO$ ratio required in the reacting fluid to remove carbon monoxide in the feed fluid for certain embodiments.

The combinations of temperature and $O_2/CO$ ratio needed to achieve carbon monoxide removal from the feed fluid containing 5 ppmv carbon monoxide in the feed fluid and less than about 0.2 ppmv carbon monoxide in the purified fluid is shown in FIG. 2. In FIG. 2, the feed fluid, for example ethylene, is assumed to comprise about 5 ppmv carbon monoxide, and the carbon monoxide in the purified fluid is selected to be less than about 0.2 ppmv. The combinations of temperature and $O_2/CO$ ratio needed to achieve this level (96%) of carbon monoxide removal are shown in FIG. 2 for space velocities of 4000 and 2000 $h^{-1}$.

Thus, carbon monoxide in the feed fluid can be effectively removed, for example 96% removal, at a temperature as low as 0° C. at high space velocity if enough oxygen, for example, an $O_2/CO$ ratio in the reacting fluid of greater than 3:1 or even 3.3:1, is present in the reacting fluid. At an operating temperature of 20° C. or higher, an $O_2/CO$ ratio of no more than 2.6 is needed. If the first packed bed were designed such that space velocity were no greater than 2000 $h^{-1}$, then the $O_2/CO$ ratio does not have to exceed 1.1 at 20° C. Thus, in any embodiments, the $O_2/CO$ molar ratio in the reacting fluid may be greater than about 1:1, 2:1, 3:1, or 3.3:1. Furthermore, in one or more embodiments, the reacting fluid is a gas, and a space velocity of the reacting fluid over the reduced copper-oxide catalyst is between about 1,000 to about 10,000 $h^{-1}$.

Given the correlations described above, and referring again to FIG. 1, in one class of embodiments, the invention provides a method of removing carbon monoxide from a feed fluid 101 comprising the steps of: providing a feed fluid 101 comprising carbon monoxide; obtaining a real-time operating temperature of a reacting fluid 105; combining an oxygen-containing fluid 103 with the feed fluid 101 to form the reacting fluid 105, wherein an amount of oxygen-containing fluid 103 combined with the feed fluid 101 is determined in real time and controlled in real time based on the real-time operating temperature of the reacting fluid 105 passing over the reduced copper-oxide catalyst, a specified carbon monoxide concentration in the feed fluid 101, and a real-time flow rate of the reacting fluid 105 over the reduced copper-oxide catalyst; and passing the reacting fluid 105 over the reduced copper-oxide catalyst to form a purified fluid 107, wherein oxygen and carbon monoxide contained in the reacting fluid 105 are reacted in the presence of the reduced copper-oxide catalyst to form carbon dioxide. In this class of embodiments, the concentration of carbon monoxide in the feed fluid 101 is assumed to be at some specified level, for example, based on feed fluid 101 specifications, historical data, off-line measurements, or other method. The specified carbon monoxide level is then used in combination with the real-time operating temperature of the reacting fluid 105 and the space velocity through the bed of catalyst to determine the amount of oxygen that should be fed to the feed fluid 101. In one or more embodiments, the optimum amount of oxygen-containing fluid 103 to add to the feed fluid 101 is calculated by Equation 4.

Another class of embodiments provides a method for olefin polymerization, comprising: providing a feed fluid 101 comprising more than about 0.2 ppm by volume of carbon monoxide; measuring an oxygen concentration and a carbon monoxide concentration in the feed fluid 101; combining an oxygen-containing fluid 103 with the feed fluid 101 to form a reacting fluid 105, wherein an amount of oxygen-containing fluid 103 combined with the feed fluid 101 is controlled to establish an $O_2/CO$ molar ratio in the reacting fluid 105 of greater than about 0.5:1; passing the reacting fluid 105 over a reduced copper-oxide catalyst at an operating temperature of less than about 40° C. to form a purified fluid 107, wherein the copper-oxide catalyst comprises copper oxide and zinc oxide, wherein oxygen and carbon monoxide contained in the reacting fluid 105 are reacted in the presence of the reduced copper-oxide catalyst to form carbon dioxide, and wherein the purified fluid 107 comprises less than about 0.2 ppm by volume of carbon monoxide; and passing the purified fluid 107 to a polymerization reactor. In one or more embodiments, the reduced copper-oxide catalyst removes oxygen in the reacting fluid 105 by reacting oxygen with the reduced copper-oxide catalyst such that the purified fluid 107 comprises less than about 0.10 ppm by volume of oxygen, and wherein the reactions of $O_2$ with CO and copper occur in a single packed bed of reduced copper-oxide catalyst.

Another class of embodiments provides a method of removing carbon monoxide from a feed fluid 101 comprising the steps of: providing a feed fluid 101 comprising carbon monoxide and oxygen; measuring an oxygen concentration and a carbon monoxide concentration in the feed fluid 101 in real time; passing the feed fluid 101 over a reduced copper-oxide catalyst to form a purified fluid 107, wherein oxygen and carbon monoxide contained in the feed fluid 101 are reacted in the presence of the reduced copper-oxide catalyst to form carbon dioxide; and controlling a real-time operating temperature of the feed fluid 101 passing over the reduced copper-oxide catalyst at a preferred operating temperature; and wherein the preferred operating temperature is determined based on a real-time molar ratio of $O_2/CO$ in the feed fluid 101 and on a real-time flow rate of the feed fluid 101 over the reduced copper-oxide catalyst. In this class of embodiments, an oxygen-containing fluid 103 may not need to be added to the feed fluid 101 as long as the $O_2/CO$ ratio is at least at the stoichiometric value. This method allows the temperature of the feed fluid 101 (in this case the feed fluid 101 is also the reacting fluid 105 discussed herein above) to be varied based on the amount of carbon monoxide and oxygen normally present in the feed fluid 101. This allows the amount of heating of the feed fluid 101 in feed heater 109 and cooling of the purified fluid 107 in purified fluid cooler 111 to be minimized to save energy. The carbon monoxide and oxygen concentrations in the feed fluid 101 may be used to determine the preferred operating temperature of the feed fluid 101 to effectively remove the carbon monoxide actually present in the feed fluid 101. In one or more embodiments, the preferred operating temperature of the feed fluid 101 may be determined by Equation 4 given above.

In one or more embodiments, the preferred operating temperature of the feed fluid 101 may be determined based the carbon monoxide and oxygen concentrations in the feed fluid 101, and a real-time flow rate of the feed fluid 101 or reacting fluid 105 over the reduced copper-oxide catalyst. In these embodiments, the correlation described in Equation 4 may be used to determine the preferred operating temperature of the feed fluid 101.

Polymerization Systems

Embodiments of the invention described herein are suitable for use in any polymerization process that facilitates the contacting of the catalyst with a monomer or monomer plus comonomer. In one or more embodiments, the polymerization system may include solution, gas-phase fluidized bed, slurry phase, a high-pressure process, or a combination thereof. One or more embodiments may include gas-phase fluidized bed or slurry phase polymerization of one or more olefins at least one of which is ethylene or propylene. The gas phase process may be a process as described in U.S. Pat. Nos. 4,543,399, 4,588,790, 5,028,670, 5,317,036, 5,352,749, 5,405,922, 5,436,304, 5,453,471, 5,462,999, 5,616,661 or 5,668,228, all of which are fully incorporated herein by reference. The polymerization processes, particularly a gas-phase fluidized bed process, may comprise a cycle fluid that comprises a gas phase and a liquid phase.

In one or more embodiments, the method of this invention may be directed toward a solution, high pressure, slurry, or gas-phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1,4-methyl-pentene-1, hexene-1, octene-1 and decene-1.

In one or more embodiments, a copolymer of ethylene is produced, where with ethylene, a comonomer having at least one alpha-olefin having from 3 to 15 carbon atoms, from 4 to 12 carbon atoms, or from 4 to 8 carbon atoms, is polymerized in a gas phase process.

The reactor pressure in a gas phase process may vary from about 100 psig (690 kPa) to about 600 psig (4138 kPa), from about 200 psig (1379 kPa) to about 400 psig (2759 kPa), or from about 250 psig (1724 kPa) to about 350 psig (2414 kPa).

The reactor temperature in a gas-phase process during the contacting step may vary in a range of from about 30° C. to about 120° C., from about 60° C. to about 115° C., from about 70° C. to 110° C., or from about 70° C. to about 95° C.

Other gas-phase processes contemplated by the method of the invention include series or multistage polymerization processes. Also gas-phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421, all of which are herein fully incorporated by reference.

In one or more embodiments, the invention is directed to a polymerization process, particularly a gas-phase or slurry phase process, for polymerizing propylene alone or with one or more other monomers including ethylene, and/or other olefins having from 4 to 12 carbon atoms. Polypropylene polymers may be produced using the bridged metallocene catalysts as described in U.S. Pat. Nos. 5,296,434 and 5,278,264, both of which are herein incorporated by reference. Propylene-based polymers that are produced in the method of the invention include atactic polypropylene, isotactic polypropylene, and syndiotactic polypropylene. Other propylene polymers include propylene random, block or impact copolymers.

In one or more embodiments, the polymerization may be by particle form polymerization, or a slurry process where the temperature is kept below the temperature at which the polymer goes into solution. Such technique is well known in the art, and described in for instance U.S. Pat. No. 3,248,179, which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. Nos. 4,613,484 and 5,986,021, which are herein fully incorporated by reference.

In other embodiments, the polymerization may be by solution processes as described in U.S. Pat. Nos. 4,271,060, 5,001,205, 5,236,998, 5,589,555 and 5,977,251, and PCT WO 99/32525 and WO 99/40130, which are fully incorporated herein by reference.

Catalyst Components And Catalyst Systems

Any polymerization catalyst suitable for use in the polymerizing olefins may be used as the polymerization process, including conventional transition metal catalysts, and metallocene catalysts.

Conventional transition metal catalysts are those traditional Ziegler-Natta catalysts and Phillips-type chromium catalyst well known in the art. Examples of conventional transition metal catalysts are discussed in U.S. Pat. Nos. 4,115,639, 4,077,904 4,482,687, 4,564,605, 4,721,763, 4,879,359 and 4,960,741, all of which are herein fully incorporated by reference. The conventional transition metal catalyst compounds that may be used in the present invention include transition metal compounds from Groups III to VIII, preferably IVB to VIB of the Periodic Table of Elements.

Still other conventional transition metal catalyst compounds and catalyst systems suitable for use in the present invention are disclosed in U.S. Pat. Nos. 4,124,532, 4,302,565, 4,302,566 and 5,763,723 and published EP-A2 0 416 815 A2 and EP-A10 420 436, which are all herein incorporated by reference.

Other catalysts may include cationic catalysts such as $AlCl_3$, vanadium, constrained-geometry catalysts, cobalt, and iron catalysts, all being well known in the art.

Metallocene catalyst compounds and catalyst systems useful in the invention may include those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517, 5,939,503 and 5,962,718 and PCT publications WO 93/08221, WO 93/08199, WO 95/07140, WO 98/11144, WO 98/41530, WO 98/41529, WO 98/46650, WO 99/02540 and WO 99/14221 and EP-A-0 578 838, EP-A-0 638 595, EP-B-0 513 380, EP-A1-0 816 372, EP-A2-0 839 834, EP-B1-0 632 819, EP-B1-0 739 361, EP-B1-0 748 821 and EP-B1-0 757 996, all of which are herein fully incorporated by reference.

Other metallocene catalysts compounds useful in the invention may include metallocene compounds described in, for example, PCT publication WO 92/00333, WO 94/07928, WO 91/04257, WO 94/03506, WO96/00244, WO 7/15602 and WO 99/20637 and U.S. Pat. Nos. 5,057,475, 5,096,867, 5,055,438, 5,198,401, 5,227,440, 5,264,405 and EP-A-0 420 436, all of which are herein fully incorporated by reference.

Furthermore, the metallocene catalyst compounds useful in the invention may include complexes of $Ni^{2+}$ and $Pd^{2+}$ described in the articles Johnson, et al., "New Pd(II)- and Ni(II)-Based Catalysts for Polymerization of Ethylene and α-Olefins", *J. Am. Chem. Soc.*, (1995) 117, 6414-6415 and Johnson et al., "Copolymerization of Ethylene and Propylene with Functionalized Vinyl Monomers by Palladium(II) Catalysts", *J. Am. Chem. Soc.*, (1996) 118, 267-268, and WO 96/23010, WO 99/02472, U.S. Pat. Nos. 5,852,145, 5,866,663 and 5,880,241, which are all herein fully incorporated by reference.

Also included as metallocene catalyst are those diimine based ligands of Group 8 to 10 metal compounds disclosed in WO 96/23010 and WO 97/48735 and Gibson et. al., *Chem. Comm.*, pp. 849-850 (1998), all of which are herein incorporated by reference.

Other metallocene catalysts are those Group 5 and 6 metal imido complexes described in EP-A2-0 816 384 and U.S. Pat. No. 5,851,945, which is incorporated herein by reference. In addition, metallocene catalysts include bridged bis(arylamido) Group 4 compounds described by D. H. McConville et al., in *Organometallics*, 1195, 14, 5478-5480, which is herein incorporated by reference. In addition, bridged bis(amido) catalyst compounds are described in WO 96/27439, which is herein incorporated by reference. Other metallocene catalysts are described as bis(hydroxy aromatic nitrogen ligands) in U.S. Pat. No. 5,852,146, which is incorporated herein by reference. Other metallocene catalysts containing one or more Group 15 atoms include those described in WO 98/46651, which is herein incorporated herein by reference. Still another metallocene catalysts include those multinuclear metallocene catalysts as described in WO 99/20665, which is incorporated herein by reference.

It is also contemplated that the metallocene catalysts described above may include their structural or optical or enantiomeric isomers (meso and racemic isomers, for example see U.S. Pat. No. 5,852,143, incorporated herein by reference) and mixtures thereof.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description of how to make and use embodiments of the invention, and are not intended to limit the scope of that which the inventors regard as their invention.

Testing was carried out in a continuous flow system through a packed bed of copper-oxide catalyst. The Test Column was a 2-inch diameter vessel. It was charged with 4195 grams of UT-2000, a copper-oxide and zinc-oxide based catalyst, creating a 5-foot-long packed bed. Six inches of ceramic balls were placed above and below the UT-2000. The UT-2000 comprised 40 wt % copper (as copper oxide), zinc oxide, alumina, and 2 wt % graphite. The catalyst particles were cylindrical tablets, 5 mm diameter by 3 mm thick with a bulk density of 1100-1300 kg/m³ (69-81 lb/cu ft). The bed voidage was about 43%. Crush Strength of the catalyst was about 30 N minimum (6.7 lb$_f$/minimum). The pore volume of the catalyst was about 0.22-0.35 ml/g and the BET surface area was about 50-90 m$^2$/g, 85 m$^2$/g typical. The feed fluid was ethylene. A heating coil and control system permitted adjustment of the ethylene temperature. Analysis of carbon monoxide and carbon dioxide at the inlet and outlet of the column was carried out every 12 minutes using a gas chromatograph with flame ionization detector and methanator. The lower limit of detection was 0.15 ppmv. Oxygen was measured at the column inlet, and intermittently at the outlet using a Delta F NANOTrace II oxygen analyzer.

In all tests, a controlled flow of unpurified ethylene was heated to the desired temperature and passed downward through the column. Ethylene exiting the column was reduced in pressure and vented to the flare. Pressure was in the range of 470 to 540 psig. The unpurified ethylene had undetectable levels of carbon monoxide and less than 0.01 ppmv of oxygen. Therefore, desired amounts of these impurities were metered with Brooks mass flow controllers into the ethylene before the Test Column. Gas cylinders of 1 vol % carbon monoxide in N$_2$ and of 0.25 vol % oxygen in N$_2$ were the sources of these feeds.

Prior to the experiments, the copper oxide in the UT-2000 was fully reduced with dilute hydrogen by: 1) heating the packed bed to 150° C. by passing a hot nitrogen stream through the packed bed; 2) feeding hydrogen at a concentration of 1.5 mol % in the nitrogen stream until an exotherm passed through the bed; 3) increasing temperature to 210° C.; and 4) increasing the hydrogen concentration in the nitrogen stream to 6 mol % and continuing the reduction until there was no evidence of an exotherm.

Experimental conditions for each test are listed in Table 1 along with measured carbon monoxide concentration in the outlet. Carbon monoxide was added to the ethylene to simulate an ethylene stream contaminated with carbon monoxide by adding a stream of nitrogen comprising 1.00 volume percent carbon monoxide to the ethylene feed fluid upstream of the analyzer sample point. Oxygen was added to the ethylene upstream of the analyzer sample point by adding a stream of nitrogen comprising 0.25 volume percent oxygen. The concentrations listed in Table 1 were determined by gas analysis.

Two periods of measurement of oxygen in the outlet during the experiments confirmed that oxygen was being removed to below detectable levels.

TABLE 1

CO Removal by Oxidation over UT-2000

| Test Date & No. | Temp ° C. | Gauge Pres kg/cm$^2$ (psi) | C$_2$H$_4$ Flow kg/h (lb/h) | Space Vel. h$^{-1}$ | Inlet O$_2$ Flow g/h (lb/h) | Inlet CO Flow g/h (lb/h) | Inlet O$_2$ Conc ppmv | Inlet CO conc ppmv | O$_2$/CO Mol/mol | Outlet CO conc ppmv | % CO removed |
|---|---|---|---|---|---|---|---|---|---|---|---|
| 1-23 01 | 35 | 34.5 (490) | 16.59 (36.5) | 4292 | 29.1 (0.064) | 7.3 (0.016) | 3.33 | 4.3 | 0.77 | 0.80 | 81 |
| 1-23 02 | 35 | 34.5 (490) | 16.54 36.4 | 4280 | 58.2 (0.128) | 7.3 (0.016) | 6.72 | 4.41 | 1.52 | 0.29 | 93 |
| 1-24 01 | 35 | 34.5 (490) | 16.453 6.2 | 4257 | 29.1 (0.064) | 7.3 (0.016) | 3.46 | 4.48 | 0.77 | 0.77 | 83 |
| 1-24 02 | 16 | 34.5 (490) | 17.733 9.0 | 4586 | 29.1 (0.064) | 7.3 (0.016) | 3.23 | 4.2 | 0.77 | 1.36 | 68 |
| 1-25 01 | 35 | 34.5 (490) | 16.18 (35.6) | 4186 | 58.2 (0.128) | 7.3 (0.016) | 6.99 | 4.58 | 1.53 | 0.41 | 91 |
| 1-25 02 | 35 | 34.5 (490) | 16.18 (35.6) | 4186 | 58.2 (0.128) | 3.6 (0.008) | 7.05 | 2.24 | 3.15 | <0.15 | 100 |
| 1-25 03 | 35 | 34.5 (490) | 16.18 (35.6) | 4186 | 29.1 (0.064) | 3.6 (0.008) | 3.50 | 2.24 | 1.56 | 0.24 | 89 |
| 1-26 01 | 25 | 34.5 (490) | 16.18 (35.6) | 4186 | 58.2 (0.128) | 3.6 (0.008) | 6.83 | 2.24 | 3.05 | <0.15 | 100 |
| 1-26 02 | 25 | 34.5 (490) | 16.45 (36.2) | 4257 | 29.1 (0.064) | 3.6 (0.008) | 3.43 | 2.18 | 1.57 | 0.29 | 87 |
| 1-26 03 | 23 | 38.0 (540) | 7.64 (16.8) | 1975 | 29.1 (0.064) | 3.6 (0.008) | 7.61 | 4.8 | 1.59 | 0.10 | 98 |
| 1-26 04 | 32 | 38.0 (540) | 7.27 (16.0) | 1881 | 14.5 (0.032) | 3.6 (0.008) | 3.80 | 4.9 | 0.77 | <0.15 | 100 |
| 1-29 01 | 15 | 33.2 (472) | 18.14 (39.9) | 4692 | 58.2 (0.128) | 7.3 (0.016) | 6.33 | 4.04 | 1.57 | 0.56 | 86 |
| 1-29 02 | 14 | 33.2 (472) | 18.45 (40.6) | 4774 | 58.2 (0.128) | 3.6 (0.008) | 6.36 | 1.95 | 3.26 | 0.15 | 92 |
| 1-30 01 | 15 | 33.2 (472) | 17.91 (39.4) | 4633 | 14.5 (0.032) | 1.8 (0.004) | 1.59 | 0.88 | 1.80 | 0.21 | 76 |
| 1-30 02 | 25 | 33.2 (472) | 16.95 (37.3) | 4386 | 14.5 (0.032) | 1.8 (0.004) | 1.64 | 0.89 | 1.85 | 0.15 | 83 |
| 1-30 03 | 15 | 33.2 (472) | 7.59 (16.7) | 1964 | 29.1 (0.064) | 3.6 (0.008) | 7.34 | 4.56 | 1.61 | 0.23 | 95 |
| 1-31 01 | 14 | 33.2 (472) | 8.82 (19.4) | 2281 | 29.1 (0.064) | 1.8 (0.004) | 6.19 | 1.82 | 3.40 | <0.15 | 100 |
| 1-31 02 | 33 | 37.3 (530) | 8.77 (19.3) | 2269 | 7.3 (0.016) | 1.8 (0.004) | 1.54 | 1.83 | 0.84 | <0.15 | 100 |
| 1-31 03 | 0 | 37.3 (530) | 9.05 (19.9) | 2340 | 7.3 (0.016) | 1.8 (0.004) | 1.44 | 1.72 | 0.84 | 0.31 | 82 |

Figure 3:
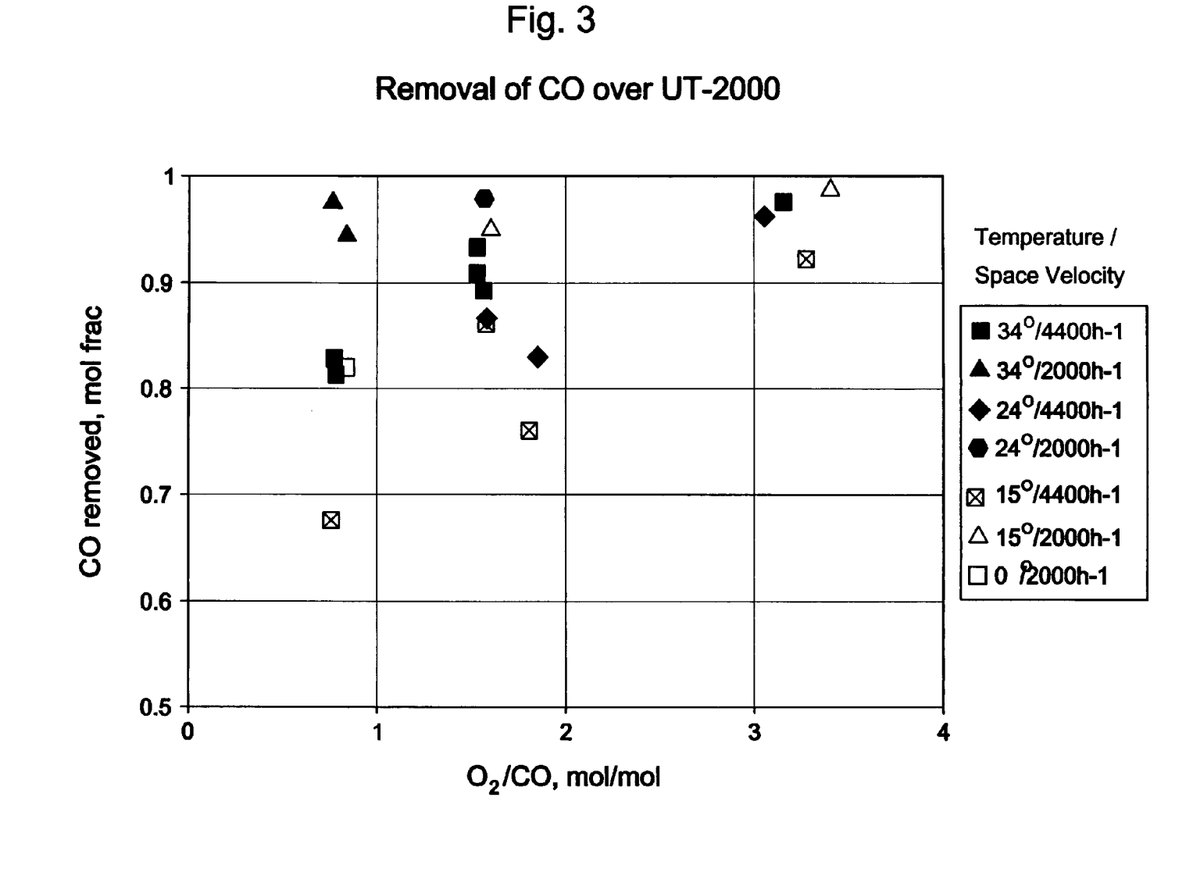
FIG. 3 is a graph of the experimental results showing the fraction of carbon monoxide removed from the feed fluid at various $O_2/CO$ ratios in the reacting fluid and space velocities through the packed bed.

The resulting data showing the percent of CO removed by the bed is plotted as a function of $O_2/CO$ ratio in FIG. 3. The data was plotted for various feed fluid temperatures and space velocities of fluid flow through the packed bed. The plot clearly indicates that carbon monoxide removal was enhanced at higher $O_2/CO$ ratio, higher temperature, and lower space velocity. Carbon monoxide was removed to less than the detectable limit of 0.15 ppmv under a variety of process conditions, including temperature less than 15° C.

Test Chronology and Observations

Figure 4:
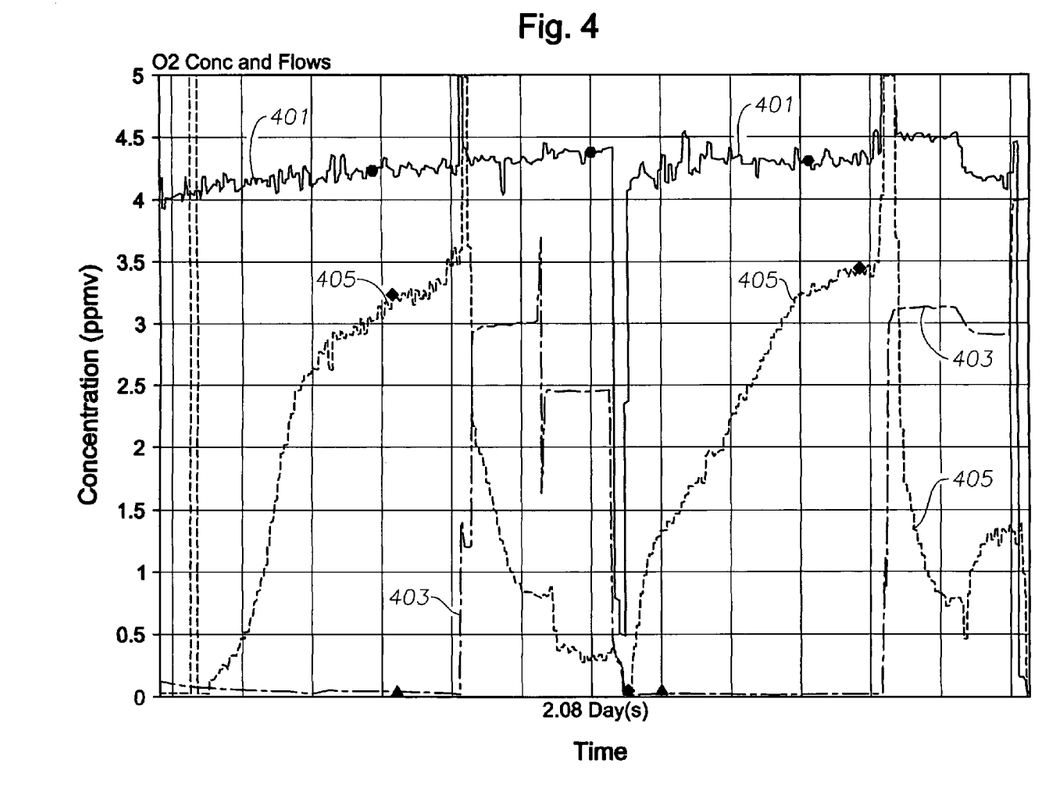
FIG. 4 is a graph of the experimental results showing carbon monoxide, oxygen, and carbon dioxide in the reacting fluid and carbon monoxide and carbon dioxide in the purified fluid.

Testing began by establishing an ethylene flow rate of 38 lb/h at a column pressure of 490 psig and a temperature of 36° C. Measurements of concentrations of carbon monoxide and oxygen in the reacting fluid and purified fluid during the test period are shown graphically in FIG. 4. FIG. 4 shows a concentration of carbon monoxide in the reacting fluid ($CO_{in}$) 401, a concentration of oxygen in the feed fluid ($O_{2in}$) 403, and a concentration of carbon monoxide in the purified fluid ($CO_{out}$) 405. The concentrations are all graphed as a parts per million by volume scale on the y axis over time in the X axis. The data for this graph was collected over a time span of 2.08 days. A flow of carbon monoxide was initiated at a rate to generate 4.0 ppmv carbon monoxide in the inlet ethylene. Breakthrough of carbon monoxide began 2.5 hours later. Eighteen hours after carbon monoxide first entered the column, its concentration at the outlet was close to 4 ppmv. These observations showed that capacity of the reduced UT-2000 for carbon monoxide removal was minimal when no oxygen was present.

Next, oxygen was fed at a rate to generate 3.0 ppmv in the inlet ethylene. Within 30 minutes after it was observed at the inlet, the carbon monoxide level at the outlet began to drop. Thus, the effect of using oxygen to remove the carbon monoxide was clearly established. Following several such experiments, oxygen was again shut off overnight while carbon monoxide continued to be fed to the column. Again, the carbon monoxide concentration at the column outlet slowly increased toward the inlet concentration. Two days of results are shown in FIG. 4, illustrating the behavior of carbon monoxide as oxygen was turned on and off.

Effect of Process Variables

The results in FIG. 3 show that the reaction of carbon monoxide with oxygen is accelerated by higher $O_2/CO$ ratio, higher temperature, and lower space velocity. In order to quantify these effects, an empirical model was developed, the result of which are presented in Equation 4.

Using the correlation of Equation 4, it can be seen that carbon monoxide can be effectively removed at a temperature as low as 0° C. at high space velocity if enough oxygen ($O_2/CO$ greater than about 3:1) is added to or is present in the ethylene. At a preferred operating temperature of 20° C. or higher, an $O_2/CO$ ratio of no more than 2.6 would be needed. If the purification bed were designed such that space velocity were no greater than 2000 $h^{-1}$ then the $O_2/CO$ ratio would not have to exceed 1.1 at 20° C.

The phrases, unless otherwise specified, "consists essentially of" and "consisting essentially of" do not exclude the presence of other steps, elements, or materials, whether or not, specifically mentioned in this specification, as along as such steps, elements, or materials, do not affect the basic and novel characteristics of the invention, additionally, they do not exclude impurities normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc. are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A method of removing carbon monoxide from a feed fluid comprising the steps of:
   a) providing a reduced copper oxide catalyst and providing a feed fluid comprising carbon monoxide and at least one olefin monomer having 2 to 10 carbon atoms;
   b) measuring an oxygen concentration and a carbon monoxide concentration in the feed fluid or in a reacting fluid;
   c) combining an oxygen-containing fluid with the feed fluid to form the reacting fluid, wherein an amount of oxygen-containing fluid combined with the feed fluid is controlled to establish an O2/CO molar ratio in the reacting fluid of greater than 2:1; and
   d) passing the reacting fluid over the reduced copper-oxide catalyst at an operating temperature of less than 40° C. to form a purified fluid, wherein oxygen and carbon monoxide contained in the reacting fluid are reacted in the presence of the reduced copper-oxide catalyst to form carbon dioxide, and wherein the reduced copper-oxide catalyst comprises copper oxide and zinc oxide.

2. The method of claim 1, wherein the amount of oxygen-containing fluid combined with the feed fluid is controlled in real-time and wherein the method further comprises:
   e) measuring a real-time carbon monoxide concentration in the purified fluid; and
   f) increasing the amount of oxygen-containing fluid combined with the feed fluid in response to an increase over time in the real-time carbon monoxide concentration measured in the purified fluid.

3. The method of claim 1, wherein the reduced copper-oxide catalyst also removes oxygen in the reacting fluid by reacting oxygen with the reduced copper-oxide catalyst such that the purified fluid comprises less than 0.20 ppm by volume of oxygen.

4. The method of claim 3, wherein the reactions of oxygen with carbon monoxide and reduced copper occur in a single packed bed of reduced copper-oxide catalyst.

5. The method of claim 1, wherein the $O_2CO$ molar ratio in the reacting fluid is equal to or greater than 3:1.

6. The method of claim 1, wherein the reacting fluid is a gas, and a space velocity of the reacting fluid over the reduced copper-oxide catalyst is between 1,000 to 10,000 $h^{-1}$.

7. The method of claim 1, wherein the operating temperature is less than 35° C.

8. The method of claim 1, wherein the purified fluid comprises less than 0.20 ppm by volume of carbon monoxide.

9. The method of claim 1, wherein the purified fluid comprises less than 0.10 ppm by volume of carbon monoxide and less than 0.10 ppm by volume of oxygen.

10. The method of claim 1, wherein the feed fluid comprises ethylene, propylene, or nitrogen.

11. A method of claim 1, further comprising passing the purified fluid to a polymerization reactor.

12. The method of claim 1, wherein the operating temperature is between 0 and 30° C.

13. The method of claim 1, wherein the $O_2/CO$ molar ratio in the reacting fluid is equal to or greater 3.3:1.

* * * * *